United States Patent
Kaneko et al.

(10) Patent No.: US 11,752,076 B2
(45) Date of Patent: Sep. 12, 2023

(54) COSMETIC

(71) Applicant: KOSE Corporation, Tokyo (JP)

(72) Inventors: Arisa Kaneko, Tokyo (JP); Shinsuke Muramatsu, Tokyo (JP)

(73) Assignee: KOSE Corporation, Tokyo (JP)

( * ) Notice: Subject to any disclaimer, the term of this patent is extended or adjusted under 35 U.S.C. 154(b) by 205 days.

(21) Appl. No.: 17/043,652

(22) PCT Filed: Mar. 22, 2019

(86) PCT No.: PCT/JP2019/012247
§ 371 (c)(1),
(2) Date: Sep. 30, 2020

(87) PCT Pub. No.: WO2019/188842
PCT Pub. Date: Oct. 3, 2019

(65) Prior Publication Data
US 2021/0022974 A1    Jan. 28, 2021

(30) Foreign Application Priority Data

Mar. 30, 2018 (JP) .................. 2018-070003

(51) Int. Cl.
| | |
|---|---|
| *A61K 8/29* | (2006.01) |
| *A61K 8/02* | (2006.01) |
| *A61K 8/06* | (2006.01) |
| *A61K 8/27* | (2006.01) |
| *A61K 8/81* | (2006.01) |
| *A61K 8/891* | (2006.01) |
| *A61Q 17/04* | (2006.01) |

(52) U.S. Cl.
CPC ............. *A61K 8/29* (2013.01); *A61K 8/0241* (2013.01); *A61K 8/064* (2013.01); *A61K 8/27* (2013.01); *A61K 8/8147* (2013.01); *A61K 8/891* (2013.01); *A61Q 17/04* (2013.01)

(58) Field of Classification Search
CPC ........ A61K 8/29; A61K 8/0241; A61K 8/064; A61K 8/27; A61K 8/8147; A61K 8/891; A61Q 17/04
See application file for complete search history.

(56) References Cited

U.S. PATENT DOCUMENTS

2014/0112965 A1    4/2014 Nakamura et al.
2016/0303032 A1*  10/2016 Kamei ................... A61K 8/19

FOREIGN PATENT DOCUMENTS

| CN | 105848633 A | 8/2016 |
| EP | 1481660 B1 | 2/2008 |
| JP | H11343222 A | 12/1999 |

(Continued)

OTHER PUBLICATIONS

Machine Translation of JP 4573383 B2 from FIT via PE2E, 2010 (Year: 2010).*

(Continued)

*Primary Examiner* — Bethany P Barham
*Assistant Examiner* — Ayaan A Alam
(74) *Attorney, Agent, or Firm* — KENJA IP LAW PC

(57) ABSTRACT

Provided is a cosmetic excelling in terms of reduction of oil weight, reduction of powder weight, improvement of dispersion stability, and dispersion stability. The cosmetic contains a metal oxide having an average particle diameter of 0.01 μm to 0.1 μm, a paste oil including a hydrophilic group, and an acrylates/ethylhexyl acrylate/dimethicone methacrylate copolymer.

6 Claims, 1 Drawing Sheet

Example 3
Dispersion stability: A judgment

Comparative Example 1
Dispersion stability: C judgment

(56) References Cited

FOREIGN PATENT DOCUMENTS

| | | | |
|---|---|---|---|
| JP | 2006523735 | A | 10/2006 |
| JP | 4573383 | B2 * | 11/2010 |
| JP | 2011079941 | A | 4/2011 |
| JP | 2013112614 | A | 6/2013 |
| JP | 2014084251 | A | 5/2014 |
| JP | 2015168642 | A | 9/2015 |
| JP | 2017114774 | A | 6/2017 |
| JP | 2018002664 | A | 1/2018 |
| WO | 2017110535 | A1 | 6/2017 |

OTHER PUBLICATIONS

Jun. 18, 2019, International Search Report issued in the International Patent Application No. PCT/JP2019/012247.

Oct. 6, 2020, International Preliminary Report on Patentability issued in the International Patent Application No. PCT/JP2019/012247.

Aug. 22, 2022, Office Action issued by the China National Intellectual Property Administration in the corresponding Chinese Patent Application No. 201980023468.3.

Nov. 8, 2022, Notification of Reasons for Refusal issued by the Japan Patent Office in the corresponding Japanese Patent Application No. 2020-509992.

Jul. 22, 2022, Office Action issued by the Taiwan Intellectual Property Office in the corresponding Taiwanese Patent Application No. 108111100.

Feb. 8, 2023, Office Action issued by the China National Intellectual Property Administration in the corresponding Chinese Patent Application No. 201980023468.3.

Jun. 22, 2023, Office Action issued by the China National Intellectual Property Administration in the corresponding Chinese Patent Application No. 201980023468.3.

* cited by examiner

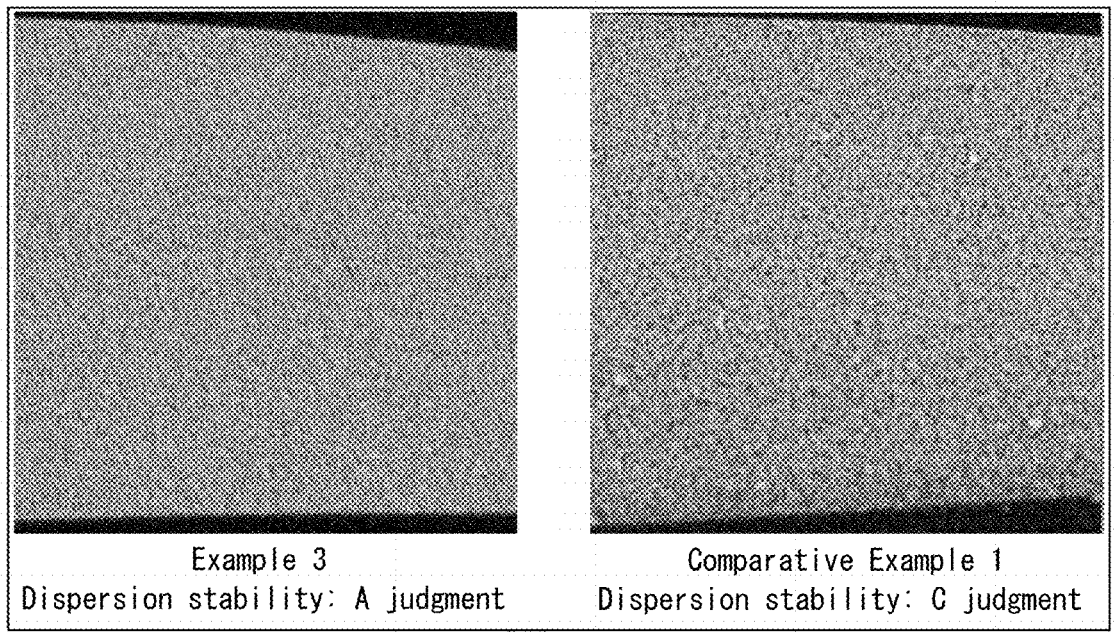

COSMETIC

TECHNICAL FIELD

The present disclosure relates to a cosmetic containing a metal oxide having an average particle diameter of 0.01 μm to 0.1 μm, a paste oil including a hydrophilic group, and an acrylates/ethylhexyl acrylate/dimethicone methacrylate copolymer. More specifically, the present disclosure relates to a cosmetic that excels in terms of reduction of oil weight, reduction of powder weight, improvement of dispersion stability, and uniformity of a cosmetic film.

BACKGROUND

In recent years, there has been demand to provide an effect of ultraviolet protection in makeup cosmetics, and the use of ultraviolet screening agents and the like that block UVA (wavelength: 320 nm to 400 nm) and UVB (wavelength: 290 nm to 320 nm) in order to impart an effect of ultraviolet protection is a known technique for preventing ultraviolet from affecting skin. Moreover, studies are being carried out in relation to a technique of using fine particulate metal oxides as ultraviolet screening agents in order to improve ultraviolet protection ability while also providing a transparent finish without whitening (for example, refer to Patent Literature (PTL) 1).

CITATION LIST

Patent Literature

PTL 1: JP2015-168642A

SUMMARY

Technical Problem

However, when the technique of PTL 1 is adopted in order to obtain a cosmetic having excellent ultraviolet protection ability and transparency, the strength of cohesive force of the fine particulate metal oxide may cause powder weight to become apparent on skin and result in poor feel. Moreover, when a water-in-oil emulsion composition is produced using the technique of PTL 1, dispersion stability tends to be poor due to cohesive force of the fine particulate metal oxide, and satisfactory uniformity of a cosmetic film may not be obtained.

Accordingly, an object of the present disclosure is to provide a cosmetic that contains an ultraviolet screening agent while also excelling in terms of lack of powder weight, lack of oil weight, cosmetic film uniformity, and dispersion stability on skin.

Solution to Problem

As a result of diligent research conducted in light of the circumstances set forth above, the inventors discovered that a cosmetic excelling in terms of lack of powder weight and uniformity of a cosmetic film on skin can be obtained through the inclusion of a paste oil including a hydrophilic group in a cosmetic that contains a metal oxide having an average particle diameter of 0.01 μm to 0.1 μm and also discovered that oil weight and reduction of dispersion stability resulting from inclusion of the paste oil including a hydrophilic group can be ameliorated through the inclusion of an acrylates/ethylhexyl acrylate/dimethicone methacrylate copolymer. In this manner, the inventors completed the present disclosure.

Specifically, the present disclosure relates to a cosmetic comprising ingredients (A) to (C):

(A) a metal oxide having an average particle diameter of 0.01 μm to 0.1 μm;

(B) an oil that is a paste at 25° C. and that includes a hydrophilic group; and (C) an acrylates/ethylhexyl acrylate/dimethicone methacrylate copolymer.

The present disclosure also relates to the cosmetic set forth above in a case in which the ingredient (A) is one type or two or more types selected from titanium oxide and zinc oxide.

The present disclosure also relates to the cosmetic set forth above in a case in which the ingredient (B) is one type or two or more types selected from N-acyl amino acid esters, glycerin fatty acid esters, dimer acid esters, and dipentaerythritol fatty acid esters.

The present disclosure also relates to the cosmetic set forth above in a case in which the ingredient (B) is one type or two or more types selected from glycerin fatty acid esters, dimer acid esters, and dipentaerythritol fatty acid esters.

The present disclosure also relates to the cosmetic set forth above in a case in which a mass content ratio of the ingredient (B) and the ingredient (C) is (B)/(C)=0.3 to 30.

The present disclosure also relates to the cosmetic set forth above in a case in which the cosmetic is a water-in-oil cosmetic.

Advantageous Effect

The present disclosure provides a cosmetic excelling in terms of lack of powder weight, lack of oil weight, uniformity of a cosmetic film, and dispersion stability.

BRIEF DESCRIPTION OF THE DRAWING

In the accompanying drawing,

FIG. 1 presents photographs of coating films in Example 3 and Comparative Example 1 after these coating films had been left for 3 hours.

DETAILED DESCRIPTION

The following provides a detailed description of the presently disclosed cosmetic. Note that "to" as used in the present specification indicates a range that is inclusive of the values before and after "to".

The metal oxide having an average particle diameter of 0.01 μm to 0.1 μm of the ingredient (A) used in the presently disclosed cosmetic is not specifically limited so long as it is a metal oxide that is used in cosmetics and may be any metal oxide regardless of particle shape (spherical, needle, plate, irregular, etc.), particle structure (porous, non-porous, etc.), and so forth. Examples of the metal oxide include zinc oxide, titanium oxide, cerium oxide, zirconium oxide, and iron oxide. One type or a combination of two or more types of these metal oxides may be used. Of these metal oxides, one type or a combination of two or more types of zinc oxide and/or titanium oxide is more preferable from a viewpoint of having excellent ultraviolet protection ability. These metal oxides may be subjected to surface treatment using one type or two or more types of fluorine compounds, silicone compounds, metallic soaps, lecithin, hydrogenated lecithin, collagen, hydrocarbons, higher fatty acids, higher alcohols, esters, waxes, surfactants, or the like.

The "average particle diameter" is the median diameter D50 determined through measurement by an image analyzer (LUZEX IIIU or the successor model LUZEX AP produced by Nireco Corporation). Note that in the case of a needle shape having a major diameter and a minor diameter, the median diameter D50 determined from a minor diameter distribution is taken to be the average particle diameter because the minor diameter is important when taking into account transparency and ultraviolet protection ability. The metal oxide may be considered to have a needle shape in a case in which the ratio of major diameter and minor diameter (major diameter/minor diameter) measured for 50 arbitrarily selected particles of the metal oxide from an image obtained by the aforementioned image analyzer has an average value of 3.0 or more. Also note that for particles having a shape other than a perfect circle in an obtained image, the median diameter may be determined using the minor diameter.

The average particle diameter of the metal oxide of the ingredient (A) used in the presently disclosed cosmetic is 0.01 μm to 0.1 μm and, although not specifically limited thereto, is more preferably 0.01 μm to 0.08 μm, and particularly preferably 0.02 μm to 0.04 μm from viewpoints such as having even better transparency and ultraviolet protection ability. Satisfactory dispersion stability cannot be obtained when the average particle diameter is less than 0.01 μm due to strong cohesive force and strong squeakiness, whereas satisfactory transparency cannot be obtained when the average particle diameter is more than 0.1 μm.

Examples of commercially available products that can be used as the ingredient (A) include fine particulate zinc oxide such as FINEX-50 (produced by Sakai Chemical Industry Co., Ltd.), XZ-100F (produced by Sakai Chemical Industry Co., Ltd.), ZnO-350 (produced by Sumitomo Osaka Cement Co., Ltd.), ZINC OXIDE FZO-50 (produced by Ishihara Sangyo Kaisha, Ltd.), and MICRO ZINC OXIDE MZ-500, MZ-300, MZ-200, and MZ-150 (produced by Tayca Corporation), fine particulate titanium oxide such as MT-700B and MT-500B (produced by Tayca Corporation), TTO-55(A) (produced by Ishihara Sangyo Kaisha, Ltd.), SMT-500SAS (produced by Tayca Corporation), MICRO TITANIUM DIOXIDE MT-500SA (produced by Tayca Corporation), ST-605EC and ST-405EC (produced by Titan Kogyo, Ltd.), and STR-100A (produced by Sakai Chemical Industry Co., Ltd.), and iron oxide such as the TAROX series (produced by Titan Kogyo, Ltd.; various types of P and HP grades: TAROX R-516P, TAROX R-516HP, TAROX YP1200P, TAROX LL100P, TAROX LL100HP, ABL-412HP, TRY-100HP, TRR-100HP, etc., and composite powders thereof). One type or a combination of two or more types of these metal oxides may be used.

Although no specific limitations are placed on the content of the ingredient (A) used in the presently disclosed cosmetic, from viewpoints such as having ultraviolet protection ability while also further excelling in terms of lack of powder weight and imparting transparency without whitening, the lower limit for the content of the ingredient (A) in the total amount of the cosmetic is preferably 0.1 mass % or more (hereinafter, simply indicated as "%"), more preferably 1% or more, and even more preferably 5% or more, the upper limit for the content of the ingredient (A) in the total amount of the cosmetic is 25% or less, more preferably 20% or less, and even more preferably 15% or less, and the range for the content of the ingredient (A) in the total amount of the cosmetic is preferably 0.1% to 25%, more preferably 1% to 15%, and even more preferably 5% to 15%.

The ingredient (B) (oil that is a paste at 25° C. and that includes a hydrophilic group) used in the presently disclosed cosmetic is an oil having a melting point at a temperature of higher than 25° C. Although not specifically limited thereto, an oil having a melting point of 25° C. to 60° C. is more preferable, and an oil having a melting point of 30° C. to 55° C. is particularly preferable. The ingredient (B) described above may be any such ingredient that can be used in cosmetics or the like and may, for example, be a vegetable oil, an animal oil, or an ester compound of a fatty acid with an ingredient including a hydrophilic group (for example, a hydroxyl group, carboxyl group, amino group, etc.) such as a higher alcohol, sterol, a sugar, a polyhydric alcohol, an amino acid, or castor oil. An oil having a section that is not completely substituted is preferable. Although no specific limitations are placed on the degree of substitution, a degree of substitution of 50 mol % or more is preferable in a case in which hydrolysis is performed and then the molar ratio of substituents relative to theoretical hydrophilic groups is measured. The ingredient (B) described above is, more specifically, preferably an N-acyl amino acid ester, a glycerin fatty acid ester, a dimer acid ester, a dipentaerythritol fatty acid ester, a fatty acid cholesteryl ester, a fatty acid phytosteryl ester, or the like. More specific examples include N-acyl amino acid esters such as dioctyldodecyl N-lauroyl-L-glutamate, di(cholesteryl/octyldodecyl) N-lauroyl-L-glutamate, di(cholesteryl/behenyl/octyldodecyl) N-lauroyl-L-glutamate, and di(phytosteryl/behenyl/octyldodecyl) N-lauroyl-L-glutamate, glycerin fatty acid esters such as hexaglycerin fatty acid esters, decaglycerin fatty acid esters, glyceryl adipate/2-ethylhexanoate/stearate, hydrogenated castor oil stearate, caprylic/capric/myristic/stearic triglyceride, bi s-diglyceryl polyacyladipate-2, and hydrogenated castor oil hydroxystearate, dimer acid esters such as phytosteryl/isostearyl/cetyl/stearyl/behenyl dimer dilinoleate, di(isostearyl/phytosteryl) dimer dilinoleate, and bis-isostearyl dimer dilinoleyl dimer dilinoleate, dipentaerythritol fatty acid esters such as dipentaerythrityl 12-hydroxystearate/stearate/rosinate, dipentaerythrityl hexahydroxystearate/hexastearate/hexarosinate, and dipentaerythrityl 12-hydroxystearate/isostearate, fatty acid cholesteryl esters such as cholesteryl isostearate, cholesteryl hydroxystearate, and cholesteryl ricinoleate, and fatty acid phytosteryl esters such as phytosteryl macadamiate. One type or two or more types of these examples may be used.

The ingredient (B) is preferably one type or two or more types selected from the group consisting of N-acyl amino acid esters, glycerin fatty acid esters, dimer acid esters, and dipentaerythritol fatty acid esters.

Of the paste oils described above, glycerin fatty acid esters, dimer acid esters, dipentaerythritol fatty acid esters, and fatty acid phytosteryl esters are more preferable. More specifically, glycerin fatty acid esters such as hexaglycerin fatty acid esters, decaglycerin fatty acid esters, glyceryl adipate/2-ethylhexanoate/stearate, hydrogenated castor oil stearate, caprylic/capric/myristic/stearic triglyceride, bis-diglyceryl polyacyladipate-2, and hydrogenated castor oil hydroxystearate, dimer acid esters such as phytosteryl/isostearyl/cetyl/stearyl/behenyl dimer dilinoleate, di(isostearyl/phytosteryl) dimer dilinoleate, and bis-isostearyl dimer dilinoleyl dimer dilinoleate, dipentaerythritol fatty acid esters such as dipentaerythrityl 12-hydroxystearate/stearate/rosinate, dipentaerythrityl hexahydroxystearate/hexastearate/hexarosinate, and dipentaerythrityl 12-hydroxystearate/isostearate, and phytosteryl macadamiate are more preferable in terms of imparting a feeling of moistness and firmness, lack of powder weight, lack of oil weight, and cosmetic film uniformity when applied onto skin.

Although no specific limitations are placed on the content of the ingredient (B) in the presently disclosed cosmetic, from viewpoints such as reduction of powder weight and uniformity of a cosmetic film, the lower limit for the content of the ingredient (B) relative to the total amount of the cosmetic is preferably 0.1% or more, more preferably 1% or more, and even more preferably 3% or more, the upper limit for the content of the ingredient (B) relative to the total amount of the cosmetic is 25% or less, more preferably 20% or less, and even more preferably 15% or less, and the range for the content of the ingredient (B) relative to the total amount of the cosmetic is preferably 0.1% to 25%, more preferably 1% to 15%, and even more preferably 3% to 15%. Reduction of powder weight is an effect that improves through increased spreadability and dispersibility due to the action of adsorption of the hydrophilic group of the ingredient (B) with the ingredient (A) or the ingredient (C). The viscosity of the ingredient (A) and the ingredient (C) readily becomes excessively low and these ingredients tend to be excessively scattered on skin through improvement of dispersibility, whereas the hydrophilic group-containing oil of (B) tends to have high viscosity due to its structure and has a characteristics of imparting a certain thickness to a cosmetic film, and thus through combined use of (A), (B), and (C), an effect of maintaining stable adhesion to skin and improving cosmetic film uniformity is obtained.

Although no specific limitations are placed on the mass content ratio of the ingredient (A) and the ingredient (B) used in the presently disclosed cosmetic, from a viewpoint of excellent solvent removal efficiency and lack of shrinkage of a molded product, (A)/(B) is preferably 0.1 to 20, more preferably 0.1 to 15, and even more preferably 0.3 to 10. The lower limit is preferably 0.1% or more, more preferably 0.3% or more, and even more preferably 3% or more, and the upper limit is 25% or less, more preferably 20% or less, and even more preferably 15% or less.

The acrylates/ethylhexyl acrylate/dimethicone methacrylate copolymer of the ingredient (C) used in the presently disclosed cosmetic is a graft copolymer formed of an acrylic polymer and dimethylpolysiloxane and has characteristics of both acrylic resin and silicone. Note that "acrylates/ethylhexyl acrylate/dimethicone methacrylate copolymer" is the INCI name (International Nomenclature Cosmetic Ingredient labeling name). Although no specific limitations are placed on the properties of the acrylates/ethylhexyl acrylate/dimethicone methacrylate copolymer, it is preferable that an acrylates/ethylhexyl acrylate/dimethicone methacrylate copolymer that is a liquid at 25° C. is used. Examples of commercially available products that can be used include KP-578 (produced by Shin-Etsu Chemical Co., Ltd.).

Although no specific limitations are placed on the content of the ingredient (C) used in the presently disclosed cosmetic, from viewpoints such as reduction of powder weight, reduction of oil weight, uniformity of a cosmetic film, and improvement of dispersion stability, the content of the ingredient (C) relative to the total amount of the cosmetic is preferably 0.1% to 10%, more preferably 0.15% to 5%, and particularly preferably 0.2% to 3%.

Although no specific limitations are placed on the mass content ratio of the ingredient (A) and the ingredient (C) used in the presently disclosed cosmetic, from viewpoints such as reduction of powder weight, reduction of oil weight, uniformity of a cosmetic film, and improvement of dispersion stability, (C)/(A) is preferably 0.01 to 2, and particularly preferably 0.1 to 1.

Although no specific limitations are placed on the mass content ratio of the ingredient (B) and the ingredient (C) used in the presently disclosed cosmetic, from viewpoints such as reduction of powder weight, reduction of oil weight, uniformity of a cosmetic film, and improvement of dispersion stability, (B)/(C) is preferably 0.2 to 30, more preferably 0.3 to 30, and particularly preferably 0.5 to 10.

In addition to the ingredients (A) to (C) described above, the presently disclosed cosmetic can contain, to a suitable extent that does not cause loss of the effects of the presently disclosed cosmetic, powders, oils, surfactants, ultraviolet absorbers, moisturizers, anti-fading agents, antioxidants, beauty ingredients, preservatives, fragrances, and so forth, depending on the objective, within quantitative and qualitative ranges that do not cause loss of the effects of the presently disclosed cosmetic.

Examples of powders other than the ingredient (A) that can be used include inorganic powders, organic powders, composite powders, and so forth without any specific limitations in terms of particle shape (spherical, needle, plate, irregular, etc.), particle diameter (fume, fine particles, pigment grade, etc.), particle structure (porous, non-porous, etc.), or the like. Specific examples include inorganic powders such as aluminum oxide, magnesium oxide, zirconium oxide, magnesium carbonate, calcium carbonate, talc, kaolin, silica, and silicon carbide, organic powders such as magnesium stearate, zinc stearate, N-acyl lysine, and nylon, white inorganic pigments such as titanium oxide, zinc oxide, cerium oxide, and barium sulfate, colored inorganic pigments such as iron oxide, carbon black, chromium oxide, chromium hydroxide, Prussian blue, ultramarine, and red iron oxide, organic pigment powders such as Red No. 201 (Pigment Red 57), Red No. 202 (Pigment Red 57:1), Red No. 205 (Pigment Red 49), Red No. 226 (Vat Red 1), Red No. 228 (Pigment Red 4), Orange No. 203 (Pigment Orange 5), Orange No. 204 (Pigment Orange 13), Blue No. 404 (Pigment Blue 15), and Yellow No. 401 (Pigment Yellow 1), organic pigment powders of zirconium, barium, or aluminum lake of Red No. 3 (Acid Red 51), Red No. 104 (Acid Red 92), Red No. 106 (Acid Red 52), Orange No. 205 (Acid Orange 7), Yellow No. 4 (Acid Yellow 23), Yellow No. 5 (Food Yellow 3), Green No. 3 (Food Green 3), Blue No. 1 (Food Blue 2), and the like, and metal powders such as aluminum powder, gold powder, and silver powder. One type or two or more types of these powders may be used. Although no specific limitations are made, from viewpoints such as reduction of powder weight, reduction of oil weight, uniformity of a cosmetic film, and improvement of dispersion stability, it is preferable that, of these powders, a white inorganic pigment such as titanium oxide, zinc oxide, cerium oxide, or barium sulfate that has a different average particle diameter to the ingredient (A) is contained in the cosmetic, and particularly preferable that titanium oxide or zinc oxide is contained in the cosmetic. One type or a composite of two or more types of these powders may be used. Moreover, a powder that has been surface treated by a commonly known method using a fluorine compound, silicone oil, metallic soap, surfactant, oil or fat, hydrocarbon, or the like may be used.

No specific limitations are placed on oils other than the ingredient (B) that can be used other than being oils that are typically used in cosmetics or the like, and examples thereof include hydrocarbons, oils and fats, waxes, hydrogenated oils, ester oils, fatty acids, higher alcohols, silicone oils, fluorine oils, lanolin derivatives, oily gelling agents, oil-soluble resins, and the like that may have properties of a solid oil, liquid oil, or volatile oil originating from an animal oil, vegetable oil, synthetic oil, or the like.

Any surfactant that is typically used in cosmetics or the like can be used and examples thereof include non-ionic surfactants, anionic surfactants, cationic surfactants, and amphoteric surfactants. Specific examples include glycerin fatty acid esters and alkylene glycol adducts thereof, polyglycerin fatty acid esters and alkylene glycol adducts thereof, sorbitan fatty acid esters and alkylene glycol adducts thereof, sucrose fatty acid esters, polyoxyethylene hydrogenated castor oil, polyoxyalkylene alkyl co-modified organopolysiloxanes, and polyether-modified organopolysiloxanes. One type or two or more types of these surfactants may be used as necessary. In a case in which a non-ionic surfactant is used in the presently disclosed cosmetic, it is preferable that a non-ionic surfactant having an HLB of 7 or less is used from a viewpoint of stability of an emulsion composition.

The presently disclosed cosmetic can be produced by a standard method without any specific limitations. For example, the cosmetic can be produced by dispersing the ingredient (A) in oil-based ingredients including the ingredient (B) and the ingredient (C), subsequently adding water-based ingredients, and emulsifying.

The presently disclosed cosmetic may, without any specific limitations, be a makeup cosmetic such as a makeup primer, foundation, eye color, lipstick, or lip cream, a skin care cosmetic such as a toner, emulsion, serum, pack, face wash, or sunscreen, a hair care cosmetic such as a shampoo, conditioner, hair pack, hair milk, hair mist, hair protecting agent, or a body care cosmetic such as a body soap or body milk. Of these examples, the presently disclosed cosmetic can suitably be used as a makeup cosmetic such as a makeup primer, foundation, eye color, lipstick, or lip cream in terms that the effects of the presently disclosed cosmetic are noticeably displayed, and is more preferably suitable as a makeup primer or foundation.

The dosage form of the presently disclosed cosmetic is not specifically limited. For example, the presently disclosed cosmetic may have an oil form, an oil-in-water form, or a water-in-oil form, and is more preferably a water-in-oil cosmetic in terms that the effects of the presently disclosed cosmetic are noticeably displayed. A propellant may be included in the presently disclosed cosmetic in order that the presently disclosed cosmetic has an aerosol dosage form or a spray dosage form. Any propellant that is typically used in cosmetics may be used without any specific limitations. Specific examples include liquefied petroleum gas, dimethyl ether, nitrogen, nitrous oxide, and carbon dioxide gas.

EXAMPLES

The following provides a more detailed description of the presently disclosed cosmetic through examples. However, the presently disclosed cosmetic is not in any way limited by these examples.

Examples 1 to 15 and Comparative Examples 1 to 3: Sunscreen

Sunscreens indicated in Table 1 were prepared and were evaluated as described below for lack of powder weight, lack of oil weight, uniformity of a cosmetic film, and dispersion stability. Judgments were made by the following judgment criteria. The results of these evaluations are also shown in Table 1.

TABLE 1

| | Ingredients | Examples | | | | | | | (Mass %) |
| | | 1 | 2 | 3 | 4 | 5 | 6 | 7 |
|---|---|---|---|---|---|---|---|---|
| 1 | Acrylates/ethylhexyl acrylate/dimethicone methacrylate copolymer *1 | 2 | 2 | 2 | 2 | 2 | 2 | 2 |
| 2 | Lauiyl polyglyceryl-3 polydimethylsiloxyethyl dimethicone *2 | — | — | — | — | — | — | — |
| 3 | Titanium oxide *3 | 10 | — | — | — | — | — | — |
| 4 | Titanium oxide *4 | — | 1 | 10 | 25 | — | — | — |
| 5 | Titanium oxide *5 | — | — | — | — | 10 | — | — |
| 6 | Zinc oxide *6 | — | — | — | — | — | 10 | — |
| 7 | Zinc oxide *7 | — | — | — | — | — | — | 10 |
| 9 | Titanium oxide *8 | — | — | — | — | — | — | — |
| 10 | Talc | Remainder | Remainder | Remainder | Remainder | Remainder | Remainder | Remainder |
| 11 | Ethylhexyl methoxycinnamate | 5 | 5 | 5 | 5 | 5 | 5 | 5 |
| 12 | Phytosteryl/isostearyl/cetyl/stearyl/behenyl dimer dilinoleate *9 | 3 | 3 | 3 | 3 | 3 | 3 | 3 |
| 13 | Bis-diglyceryl polyacyladipate-2 *10 | — | — | — | — | — | — | — |
| 14 | Capiylic/capric/myristic/stearic triglyceride *11 | — | — | — | — | — | — | — |
| 15 | Dipentaerythrityl hexahydroxystearate/hexastearate/hexarosinate *12 | — | — | — | — | — | — | — |
| 16 | Vaseline *13 | — | — | — | — | — | — | — |
| 17 | Cyclomethicone | 20 | 20 | 20 | 20 | 20 | 20 | 20 |
| 18 | Methylpolysiloxane | 5 | 5 | 5 | 5 | 5 | 5 | 5 |
| 19 | Lauryl PEG-9 polydimethylsibxyethyl dimethicone *14 | 2 | 2 | 2 | 2 | 2 | 2 | 2 |
| 20 | Water | 25 | 25 | 25 | 25 | 25 | 25 | 25 |
| 21 | Ethanol | 5 | 5 | 5 | 5 | 5 | 5 | 5 |
| 22 | 1,3-Butylene glycol | 5 | 5 | 5 | 5 | 5 | 5 | 5 |
| 23 | Sodium chloride | 0.5 | 0.5 | 0.5 | 0.5 | 0.5 | 0.5 | 0.5 |
| | Ingredient (A)/Ingredient (B) | 3.33 | 0.33 | 3.33 | 8.33 | 3.33 | 3.33 | 3.33 |

TABLE 1-continued

| | | | | | | | |
|---|---|---|---|---|---|---|---|
| Ingredient (B)/Ingredient (C) | 1.5 | 1.5 | 1.5 | 1.5 | 1.5 | 1.5 | 1.5 |
| Ingredient (A)/Ingredient (C) | 5 | 0.5 | 5 | 12.5 | 5 | 5 | 5 |
| Ingredient (C)/Ingredient (A) | 0.2 | 2 | 0.2 | 0.08 | 0.2 | 0.2 | 0.2 |
| Evaluation categories and judgments> | | | | | | | |
| Lack of powder weight | A | A | A | B | A | A | A |
| Lack of oil weight | A | B | A | A | A | A | A |
| Cosmetic film uniformity | A | A | A | A | A | A | A |
| Dispersion stability | A | A | A | A | A | A | A |

| | Ingredients | 8 | 9 | 14 | 10 | 11 | 12 (Mass %) |
|---|---|---|---|---|---|---|---|
| 1 | Acrylates/ethylhexyl acrylate/dimethicone methacrylate copolymer *1 | 0.1 | 5 | 10 | 2 | 2 | 2 |
| 2 | Lauiyl polyglyceryl-3 polydimethylsiloxyethyl dimethicone *2 | — | — | — | — | — | — |
| 3 | Titanium oxide *3 | — | — | — | — | — | — |
| 4 | Titanium oxide *4 | 10 | 10 | 10 | 10 | 10 | 10 |
| 5 | Titanium oxide *5 | — | — | — | — | — | — |
| 6 | Zinc oxide *6 | — | — | — | — | — | — |
| 7 | Zinc oxide *7 | — | — | — | — | — | — |
| 9 | Titanium oxide *8 | — | — | — | — | — | — |
| 10 | Talc | Remainder | Remainder | Remainder | Remainder | Remainder | Remainder |
| 11 | Ethylhexyl methoxycinnamate | 5 | 5 | 5 | 5 | 5 | 5 |
| 12 | Phytosteryl/isostearyl/cetyl/stearyl/behenyl dimer dilinoleate *9 | 3 | 3 | 3 | — | — | — |
| 13 | Bis-diglyceryl polyacyladipate-2 *10 | — | — | — | 3 | — | — |
| 14 | Capiylic/capric/myristic/stearic triglyceride *11 | — | — | — | — | 3 | — |
| 15 | Dipentaerythrityl hexahydroxystearate/hexastearate/hexarosinate *12 | — | — | — | — | — | 3 |
| 16 | Vaseline *13 | — | — | — | — | — | — |
| 17 | Cyclomethicone | 20 | 20 | 20 | 20 | 20 | 20 |
| 18 | Methylpolysiloxane | 5 | 5 | 5 | 5 | 5 | 5 |
| 19 | Lauryl PEG-9 polydimethylsibxyethyl dimethicone *14 | 2 | 2 | 2 | 2 | 2 | 2 |
| 20 | Water | 25 | 25 | 25 | 25 | 25 | 25 |
| 21 | Ethanol | 5 | 5 | 5 | 5 | 5 | 5 |
| 22 | 1,3-Butylene glycol | 5 | 5 | 5 | 5 | 5 | 5 |
| 23 | Sodium chloride | 0.5 | 0.5 | 0.5 | 0.5 | 0.5 | 0.5 |
| | Ingredient (A)/Ingredient (B) | 3.33 | 3.33 | 3.33 | 3.33 | 3.33 | 3.33 |
| | Ingredient (B)/Ingredient (C) | 30 | 0.6 | 0.3 | 1.5 | 1.5 | 1.5 |
| | Ingredient (A)/Ingredient (C) | 100 | 2 | 1 | 5 | 5 | 5 |
| | Ingredient (C)/Ingredient (A) | 0.01 | 0.5 | 1 | 0.2 | 0.2 | 0.2 |
| | Evaluation categories and judgments> | | | | | | |
| | Lack of powder weight | A | A | B | A | A | A |
| | Lack of oil weight | A | A | B | A | A | B |
| | Cosmetic film uniformity | B | A | B | A | A | A |
| | Dispersion stability | B | A | A | A | A | A |

| | Ingredients | 13 | 14 | 15 | 1 | 2 | 3 (Mass %) |
|---|---|---|---|---|---|---|---|
| 1 | Acrylates/ethylhexyl acrylate/dimethicone methacrylate copolymer *1 | 2 | 2 | 2 | — | 2 | 2 |
| 2 | Lauiyl polyglyceryl-3 polydimethylsiloxyethyl dimethicone *2 | — | — | — | 2 | — | — |
| 3 | Titanium oxide *3 | — | — | — | — | — | — |
| 4 | Titanium oxide *4 | 10 | 10 | 5 | 10 | 10 | 10 |
| 5 | Titanium oxide *5 | — | — | — | — | — | — |
| 6 | Zinc oxide *6 | — | — | — | — | — | — |
| 7 | Zinc oxide *7 | — | — | — | — | — | — |
| 9 | Titanium oxide *8 | — | — | 5 | — | — | — |
| 10 | Talc | Remainder | Remainder | Remainder | Remainder | Remainder | Remainder |
| 11 | Ethylhexyl methoxycinnamate | 5 | 5 | 5 | 5 | 5 | 5 |
| 12 | Phytosteryl/isostearyl/cetyl/stearyl/behenyl dimer dilinoleate *9 | 0.5 | 20 | 3 | 3 | — | — |
| 13 | Bis-diglyceryl polyacyladipate-2 *10 | — | — | — | — | — | — |
| 14 | Capiylic/capric/myristic/stearic triglyceride *11 | — | — | — | — | — | — |
| 15 | Dipentaerythrityl hexahydroxystearate/hexastearate/hexarosinate *12 | — | — | — | — | — | — |
| 16 | Vaseline *13 | — | — | — | — | — | 3 |
| 17 | Cyclomethicone | 20 | 20 | 20 | 20 | 20 | 20 |
| 18 | Methylpolysiloxane | 5 | 5 | 5 | 5 | 5 | 5 |
| 19 | Lauryl PEG-9 polydimethylsibxyethyl dimethicone *14 | 2 | 2 | 2 | 2 | 2 | 2 |
| 20 | Water | 25 | 25 | 25 | 25 | 25 | 25 |

TABLE 1-continued

| | | | | | | | |
|---|---|---|---|---|---|---|---|
| 21 | Ethanol | 5 | 5 | 5 | 5 | 5 | 5 |
| 22 | 1,3-Butylene glycol | 5 | 5 | 5 | 5 | 5 | 5 |
| 23 | Sodium chloride | 0.5 | 0.5 | 0.5 | 0.5 | 0.5 | 0.5 |
| | Ingredient (A)/Ingredient (B) | 20.00 | 0.50 | 1.66 | 3.33 | — | — |
| | Ingredient (B)/Ingredient (C) | 0.25 | 10 | 1.5 | — | — | — |
| | Ingredient (A)/Ingredient (C) | 5 | 5 | 2.5 | — | 5 | 5 |
| | Ingredient (C)/Ingredient (A) | 0.2 | 0.2 | 0.4 | — | 0.2 | 0.2 |
| | Evaluation categories and judgments> | | | | | | |
| | Lack of powder weight | B | A | A | B | C | C |
| | Lack of oil weight | A | B | A | D | B | C |
| | Cosmetic film uniformity | A | A | A | B | C | C |
| | Dispersion stability | A | A | A | C | B | B |

*1 KP-578 (produced by Shin-Etsu Chemical Co., Ltd.)
*2 KF-6105 (produced by Shin-Etsu Chemical Co., Ltd.)
*3 MT-05 (produced by Tayca Corporation; average particle diameter: 0.01 μm)
*4 MT-500B (produced by Tayca Corporation; average particle diameter: 0.035 μm)
*5 MT-700B (produced by Tayca Corporation; average particle diameter: 0.09 μm)
*6 MZ-500 (produced by Tayca Corporation; average particle diameter: 0.025 μm)
*7 MZ-200 (produced by Tayca Corporation; average particle diameter: 0.05 μm)
*8 MP-1133 (produced by Tayca Corporation; average particle diameter: 0.27 μm)
*9 PLANDOOL-S (produced by NipponFine Chemical Co., Ltd.)
*10 SOFTISAN 649 (produced by Sasol Germany GmbH)
*11 SALACOS 334 (produced by The NisshinOilliO Group, Ltd.)
*12 168ARNV (produced by The NisshinOilliO Group, Ltd.)
*13 Snowwhite Special (produced by Sonnebom)
*14 KF-6038 (produced by Shin-Etsu Chemical Co., Ltd.)

(Production Method)
A: Homogeneously mix ingredients (1) to (10), (17), and (18)
B: Homogeneously mix ingredients (11) to (16) and (19) with A
C: Add dissolved material of ingredients (20) to (23) to B and perform emulsification and mixing
D: Degas C to obtain a water-in-oil sunscreen cosmetic
(Evaluation Method)
Methods described below were used to perform evaluations for the following evaluation categories.
(Evaluation Categories)
  I. Lack of powder weight
  II. Lack of oil weight
  III. Cosmetic film uniformity
  IV. Dispersion stability
(Evaluation Method: Lack of Powder Weight, Lack of Oil Weight, and Cosmetic Film Uniformity)

A professional evaluation panel consisting of 20 members carried out a usage test for each of the sunscreen cosmetics. Each of the panel members made an evaluation using the 6 levels in the following absolute evaluations to assign an evaluation score, an average value was calculated for each sample from the total evaluation score of all of the panel members, and then a judgment was made by the following 4-level judgment criteria.

I. Lack of powder weight was evaluated by applying each sample onto skin and then evaluating whether there was a feeling of resistance due to powder on the skin.

II. Lack of oil weight was evaluated by applying each sample onto skin and then evaluating whether or not the sample could easily be spread on the skin.

III. Cosmetic film uniformity was evaluated by applying each sample onto skin and then evaluating whether or not there was non-uniformity of pigment in the finished cosmetic film.

<Evaluation Criteria>
  (Evaluation result): (Evaluation score)
  Excellent: 6 points
  Good: 5 points
  Fairly good: 4 points
  Mediocre: 3 points
  Fairly poor: 2 points
  Poor: 1 point
<4-Level Judgment Criteria>
  (Judgment): (Evaluation Criteria)
  A: 5.0 points or more
  B: Not less than 3.5 points and less than 5.0 points
  C: Not less than 2.0 points and less than 3.5 points
  D: Less than 2.0 points
(Evaluation Method: Dispersion Stability)

After placing 0.1 g of the sunscreen cosmetic on a glass plate, the film thickness thereof was adjusted to 25 μm with a doctor blade. The resultant coating film was left for 3 hours and was then visually inspected to make a judgment by the following 3-level judgment criteria. FIG. 1 illustrates the coating films in Example 3 and Comparative Example 1 after 3 hours.
<3-Level Judgment Criteria>
  (Judgment): (Evaluation Criteria)
  A: Almost no aggregates of powder observed
  B: Some aggregates of powder observed
  C: Many aggregates of powder observed As clearly shown by the results in Table 1, Examples 1 to 15 were cosmetics excelling in terms of lack of powder weight, lack of oil weight, and cosmetic film uniformity, while also having excellent dispersion stability.

On the other hand, powder dispersibility was poor and an increase in aggregates over time was observed in Comparative Example 1 in which lauryl polyglyceryl-3 polydimethylsiloxyethyl dimethicone was used instead of the ingredient (C). Moreover, oil weight originating from the ingredient (B) became apparent, and satisfactory spreading could not be achieved. In Comparative Example 2 in which the ingredient (B) was not included, oil weight was absent, the number of aggregates did not increase over time, and dispersion stability was excellent, but a small amount of powder aggregates was present straight after production, powder weight during application was accentuated, and satisfactory cosmetic film uniformity could not be achieved. In Comparative Example 3 in which a non-polar paste oil that did not include a hydrophilic group was used instead of the ingredient (B), dispersion stability over time was excellent, but, in the same way as for Comparative Example 2, a small amount of powder aggregates was observed straight after production, powder weight was apparent during application, and satisfactory cosmetic film uniformity could not be achieved. Moreover, the non-polar paste oil had poor dispersibility, resulting in accentuation of oil weight of the paste oil during application.

Example 16: Water-in-Oil Foundation

| (Ingredient) | (Mass %) |
|---|---|
| 1. Titanium oxide *4 | 20.0 |
| 2. Iron oxide | 3.0 |
| 3. Isododecane | 10.0 |
| 4. Acrylates/ethylhexyl acrylate/dimethicone methacrylate copolymer *1 | 2.0 |
| 5. Methyl trimethicone | 10.0 |
| 6. Phytosteryl/isostearyl/cetyl/stearyl/behenyl dimer dilinoleate *9 | 3.0 |
| 7. 2-Ethylhexyl para-methoxycinnamate | 5.0 |
| 8. Dimethylpolysiloxane (6 cs) | 5.0 |
| 9. Sorbitan sesquiisostearate | 0.5 |
| 10. Bis-ethylhexyloxyphenol methoxyphenyl triazine | 0.5 |
| 11. Spherical polyethylene | 3.0 |
| 12. Mica | 10.0 |
| 13. Phenylbenzimidazole sulfonic acid | 2.0 |
| 14. Ethanol | 10.0 |
| 15. Triethanolamine | 1.0 |
| 16. Ascorbic acid glucoside | 1.0 |
| 17. Purified water | Remainder |

Note that the iron oxide was a mixture of 1.0 mass % of red iron oxide (average particle diameter: 0.09 μm) and 2.0 mass % of yellow iron oxide (average particle diameter: 0.07 μm) that were added simultaneously in "A" in the following production method.

(Production Method)

A: Homogeneously disperse ingredients 1 to 4 using a three-roller mill

B: Dissolve and mix ingredients 6 to 10 at 80° C., cool to room temperature, and subsequently add and disperse A and ingredients 5, 11, and 12

C: Homogeneously mix and dissolve ingredients 13 to 17

D: Add C to B and emulsify to obtain a water-in-oil foundation

The water-in-oil foundation of Example 16 that was obtained as set forth above was a cosmetic lacking powder weight and oil weight, and having excellent cosmetic film uniformity while also having excellent dispersion stability.

Example 17: Solid Water-in-Oil Emulsion Foundation

| (Ingredient) | (Mass %) |
|---|---|
| 1. Titanium oxide *5 | 8.0 |
| 2. Acrylates/ethylhexyl acrylate/dimethicone methacrylate copolymer *1 | 2.0 |
| 3. Dimethylpolysiloxane (10 cs) | 2.0 |
| 4. Decamethylcyclopentasiloxane | 5.0 |
| 5. Phytosteryl/isostearyl/cetyl/stearyl/behenyl dimer dilinoleate *9 | 3.0 |
| 6. Isohexadecane | 10.0 |
| 7. Liquid paraffin | 5.0 |
| 8. Dextrin fatty acid ester | 2.0 |
| 9. Candelilla wax (melting point: 70° C.) | 2.0 |

-continued

| (Ingredient) | (Mass %) |
|---|---|
| 10. Stearoyl inulin | 2.0 |
| 11. Glyceryl tribehenate (melting point: 60° C.) | 2.0 |
| 12. Methylene bis-benzotriazolyl tetramethylbutylphenol | 2.0 |
| 13. Silicone-treated titanium oxide (average particle diameter: 0.035 μm) | 10.0 |
| 14. Iron oxide | 12.0 |
| 15. Silicic anhydride | 2.0 |
| 16. L-Menthol | 0.01 |
| 17. Methyl parahydroxybenzoate | 0.1 |
| 18. 1,3-Butylene glycol | 5.0 |
| 19. Sodium L-glutamate | 0.2 |
| 20. Purified water | Remainder |

Note that the iron oxide was a mixture of 4.0 mass % of red iron oxide (average particle diameter: 0.09 μm) and 8.0 mass % of yellow iron oxide (average particle diameter: 0.07 μm) that were added simultaneously in "A" in the following production method.

(Production Method)

A: Mix ingredients 1 to 15 at 75° C. using a Homo Mixer

B: Mix ingredients 16 to 20 at 70° C.

C: Gradually inject B into A and emulsify, cool to 60° C., pour into a container, and cool to room temperature to obtain a solid water-in-oil foundation The solid water-in-oil emulsion foundation of Example 17 that was obtained as set forth above was a cosmetic lacking powder weight and oil weight, and having excellent cosmetic film uniformity while also having excellent dispersion stability.

Example 18: Water-in-Oil Emulsion Blusher

| (Ingredient) | (Mass %) |
|---|---|
| 1. Amodimethicone-treated titanium oxide (average particle diameter: 0.09 μm) | 3.0 |
| 2. Red No. 226 (Vat Red 1) | 0.5 |
| 3. Yellow No. 4 (Acid Yellow 23) | 0.3 |
| 4. Dimethylpolysiloxane-treated synthetic phlogopite | 3.5 |
| 5. Acrylates/ethylhexyl acrylate/dimethicone methacrylate copolymer *1 | 2.0 |
| 6. Di-2-ethylhexyl malate | 5.0 |
| 7. Phytosteryl/isostearyl/cetyl/stearyl/behenyl dimer dilinoleate *9 | 3.0 |
| 8. Isododecane | 15.0 |
| 9. Glyceryl tripalmate | 5.0 |
| 10. Mica | 5.0 |
| 11. Astaxanthin | 0.001 |
| 12. Zinc stearate-treated synthetic phlogopite titanium | 5.0 |
| 13. Nylon powder | 3.0 |
| 14. Dimethyl distearyl ammonium hectorite | 1.0 |
| 15. Methylparaben | 0.2 |
| 16. Ethyl alcohol | 5.0 |
| 17. Glycerin | 5.0 |
| 18. Purified water | Remainder |
| 19. Fragrance | Suitable amount |
| 20. Sodium chloride | 0.3 |

(Production Method)

A: Roller process ingredients 1 to 6 to homogeneously mix ingredients

B: Mix ingredients 7 to 14 with A

C: Mix and dissolve ingredients 15 to 20

D: Add C to B, emulsify, and load into a container to obtain a water-in-oil emulsion blusher The water-in-oil emulsion blusher of Example 18 that was obtained as set forth above was a cosmetic lacking powder weight and oil weight, and having excellent cosmetic film uniformity while also having excellent dispersion stability.

Example 19: Water-in-Oil Emulsion Primer

| (Ingredient) | (Mass %) |
|---|---|
| 1. Zinc stearoyl glutamate-treated titanium oxide (average particle diameter: 0.035 μm) | 5.0 |
| 2. Red No. 226 (Vat Red 1) | 0.15 |
| 3. Stearic acid-treated yellow iron oxide (needle minor diameter: average particle diameter 0.09 μm) | 0.5 |
| 4. Isododecane | 20.0 |
| 5. Acrylates/ethylhexyl acrylate/dimethicone methacrylate copolymer *1 | 2.0 |
| 6. 2-Ethylhexyl para-methoxycinnamate | 5.0 |
| 7. Diethylamino hydroxybenzoyl hexyl benzoate | 1.0 |
| 8. Bis-ethylhexyloxyphenol methoxyphenyl triazine | 1.0 |
| 9. Glyceryl triisostearate | 5.0 |
| 10. Phytosteryl/isostearyl/cetyl/stearyl/behenyl dimer dilinoleate *9 | 3.0 |
| 11. Diphenyl dimethicone/vinyl diphenyl dimethicone/silsessquioxane crosspolymer | 3.0 |
| 12. Methyl methacrylate crosspolymer | 3.0 |
| 13. Dimethyl distearyl ammonium hectorite | 1.0 |
| 14. Methylparaben | 0.1 |
| 15. Ethyl alcohol | 5.0 |
| 16. Glycerin | 3.0 |
| 17. Rosemary extract | 0.1 |
| 18. Purified water | Remainder |
| 19. Fragrance | Suitable amount |
| 20. Sodium chloride | 1.0 |
| 21. Methylene bis-benzotriazolyl tetramethylbutylphenol | 2.0 |

(Production Method)

A: Heat ingredients 4 to 10 to 80° C., and mix and dissolve ingredients

B: Disperse ingredients 1 to 3 and 11 to 13 in A and then cool to room temperature C: Mix and dissolve ingredients 14 to 20

D: Disperse ingredient 21 in C

E: Add D to B, emulsify, and load into a container to obtain a water-in-oil emulsion primer The water-in-oil emulsion primer of Example 19 that was obtained as set forth above was a cosmetic lacking powder weight and oil weight, and having excellent cosmetic film uniformity while also having excellent dispersion stability.

Example 20: Eyebrow Cosmetic (Stick)

| (Ingredient) | (Mass %) |
|---|---|
| 1. Ceresin wax | 10.0 |
| 2. Polyethylene wax | 3.0 |
| 3. Partially crosslinked organopolysiloxane | 1.0 |
| 4. Phytosteryl/isostearyl/cetyl/stearyl/behenyl dimer dilinoleate *9 | 3.0 |
| 5. Dimethylpolysiloxane (10 cs) | 2.0 |
| 6. Isohexadecane | 20.0 |
| 7. Acrylates/dimethicone copolymer | 10.0 |
| 8. 2-Ethylhexyl para-methoxycinnamate | 5.0 |
| 9. Acrylates/ethylhexyl acrylate/dimethicone methacrylate copolymer *1 | 2.0 |
| 10. Spherical polymethyl methacrylate powder (average particle diameter: 10 μm) | 5.0 |
| 11. Mica | 5.0 |
| 12. Silicone-treated titanium oxide (average particle diameter: 0.01 μm) | 1.0 |
| 13. Silicone-treated red iron oxide (needle minor diameter: average particle diameter 0.09 μm) | 0.3 |

-continued

| (Ingredient) | (Mass %) |
|---|---|
| 14. Silicone-treated yellow iron oxide (needle minor diameter: average particle diameter: 0.07 μm) | 1.0 |
| 15. Silicone-treated black iron oxide (average particle diameter: 0.09 μm) | 0.5 |
| 16. Fumed hydrophobic silica | 1.0 |
| 17. Antioxidant (rosemary extract) | 0.3 |
| 18. Vitamin A oil | 0.5 |
| 19. Purified water | Remainder |
| 20. 1,3-Butylene glycol | 5.0 |
| 21. Carrageenan | 0.5 |
| 22. Triethanolamine | 0.1 |
| 23. Fragrance | Suitable amount |

(Production Method)

A: Homogeneously dissolve ingredients 1 to 9 at 100° C.

B: Add ingredients 10 to 18 to A and homogeneously disperse using a DESPA mixer

C: Homogeneously mix ingredients 19 to 23 and adjust to 80° C.

D: Add C to B, emulsify using a DESPA mixer, degas, pour the resultant product into a mold for stick shaping at a filling temperature of 80° C., and then cool and solidify to obtain an eyebrow cosmetic The eyebrow cosmetic of Example 20 that was obtained as set forth above was a cosmetic lacking powder weight and oil weight, and having excellent cosmetic film uniformity while also having excellent dispersion stability.

Example 21: Lipstick (Liquid)

| (Ingredient) | (Mass %) |
|---|---|
| 1. Dextrin palmitate | 5.0 |
| 2. Triethylhexanoin | 5.0 |
| 3. Phytosteryl/isostearyl/cetyl/stearyl/behenyl dimer dilinoleate *9 | 3.0 |
| 4. Isododecane | 20.0 |
| 5. Liquid lanolin | 10.0 |
| 6. Acrylates/dimethicone copolymer | 5.0 |
| 7. Acrylates/ethylhexyl acrylate/dimethicone methacrylate copolymer *1 | 2.0 |
| 8. Titanium oxide (average particle diameter: 0.035 μm) | 2.0 |
| 9. Yellow iron oxide (needle minor diameter: average particle diameter 0.07 μm) | 0.5 |
| 10. Black iron oxide (average particle diameter: more than 0.1 μm and not more than 0.3 μm) | 0.1 |
| 11. Silicone-treated iron oxide-coated mica titanium | 5.0 |
| 12. Mica | 8.0 |
| 13. Antioxidant (tocopherol acetate) | 0.5 |
| 14. Preservative (phenoxyethanol) | 0.3 |
| 15. Purified water | Remainder |
| 16. Ethyl alcohol | 3.0 |
| 17. Diglycerin | 0.5 |
| 18. Locust bean gum | 0.1 |
| 19. Glucosyl trehalose | 0.3 |

(Production Method)

A: Heat and dissolve ingredients 1 to 3 at 90° C., subsequently add ingredients 4 to 14 thereto, and homogeneously disperse using a Homo Mixer B: Homogeneously dissolve ingredients 15 to 19, subsequently add to A, and emulsify C: Degas B and then load into a container as lipstick The lipstick of Example 21 that was obtained as set forth above was a cosmetic lacking powder weight and oil weight, and having excellent cosmetic film uniformity while also having excellent dispersion stability.

Example 22: Eye Color

| (Ingredient) | (Mass %) |
|---|---|
| 1. Acrylates/dimethicone copolymer | 14.0 |
| 2. Acrylates/ethylhexyl acrylate/dimethicone methacrylate copolymer *1 | 2.0 |
| 3. Isododecane | 14.0 |
| 4. Phytosteryl/isostearyl/cetyl/stearyl/behenyl dimer dilinoleate *9 | 3.0 |
| 5. Dimethylpolysiloxane (6 cs) | 3.0 |
| 6. Silicone-treated titanium oxide (average particle diameter: 35 nm; dimethicone-treated) | 1.5 |
| 7. Red No. 226 (Vat Red 1) | 0.3 |
| 8. Red iron oxide (needle minor diameter: average particle diameter: 0.09 μm) | 0.2 |
| 9. Titanium oxide (average particle diameter: 0.035 μm) | 0.1 |
| 10. Black iron oxide (average particle diameter: more than 0.1 μm and not more than 0.3 μm) | 0.1 |
| 11. Mica | 2.0 |
| 12. Silicone-treated mica titanium | 3.0 |
| 13. Spherical nylon powder (average particle diameter: 15 μm) | 3.0 |
| 14. Purified water | Remainder |
| 15. Ethyl alcohol | 7.0 |
| 16. Glycerin | 3.0 |
| 17. Agar | 0.1 |
| 18. Preservative (phenoxyethanol) | 0.1 |
| 19. Fragrance | 0.1 |

(Production Method)

A: Homogeneously mix ingredients 1 to 13 using a Homo Mixer

B: Homogeneously dissolve and mix ingredients 14 to 19, add to A, emulsify, degas, and subsequently load into a resin container equipped with an applicator to obtain eye color The eye color of Example 22 that was obtained as set forth above was a cosmetic lacking powder weight and oil weight, and having excellent cosmetic film uniformity while also having excellent dispersion stability.

Example 23: Aerosol Sunscreen

| (Ingredient) | (Mass %) |
|---|---|
| 1. Zinc oxide *6 | 5.0 |
| 2. Titanium oxide *4 | 20.0 |
| 3. 2-Ethylhexyl methoxycinnamate | 5.0 |
| 4. Dimethicone | 5.0 |
| 5. Phytosteryl/isostearyl/cetyl/stearyl/behenyl dimer dilinoleate *9 | 3.0 |
| 6. Acrylates/ethylhexyl acrylate/dimethicone methacrylate copolymer *1 | 2.0 |
| 7. Vinylpyrrolidone-vinyl acetate copolymer | 12.0 |
| 8. Carrageenan | 0.2 |
| 9. Purified water | Remainder |

(Production Method)

A: Heat and mix ingredients 1 to 7 at 50° C. to homogeneously disperse the ingredients B: Add ingredients 8 and 9 to B, and emulsify at normal temperature to obtain a liquid concentrate C: Load 6 g of the liquid concentrate obtained in B into a pressure-resistant container made from aluminum, subsequently fix a valve, and load 6 g of LPG0.15 into the pressure-resistant container via the valve to obtain an aerosol sunscreen The aerosol sunscreen of Example 23 that was obtained as set forth above was a cosmetic lacking powder weight and oil weight, and having excellent cosmetic film uniformity while also having excellent dispersion stability.

Example 24: Aerosol Foundation

| (Ingredient) | (Mass %) |
|---|---|
| 1. Titanium oxide *5 | 20.0 |
| 2. Red iron oxide powder (needle minor diameter: average particle diameter 0.07 μm) | 0.8 |
| 3. Yellow iron oxide powder (needle minor diameter: average particle diameter 0.09 μm) | 1.5 |
| 4. Black iron oxide powder (average particle diameter: more than 0.1 μm and not more than 0.3 μm) | 0.5 |
| 5. Decamethylcyclopentasiloxane | 10.0 |
| 6. Polyglyceryl-3 polydimethylsiloxyethyl dimethicone | 1.0 |
| 7. Decamethylcyclopentasiloxane | 5.0 |
| 8. Dimethylpolysiloxane | Remainder |
| 9. Diethylamino hydroxybenzoyl hexyl benzoate | 2.0 |
| 10. 2-Ethylhexyl methoxycinnamate | 8.0 |
| 11. Alkyl benzoate | 5.0 |
| 12. Phytosteryl/isostearyl/cetyl/stearyl/behenyl dimer dilinoleate *9 | 3.0 |
| 13. Acrylates/ethylhexyl acrylate/dimethicone methacrylate copolymer *1 | 2.0 |
| 14. Mixture of partially crosslinked organopolysiloxane polymerized product | 2.0 |
| 15. Stearoxy dimethicone | 0.5 |
| 16. Agar | 0.1 |
| 17. Emulsion of bis-ethylhexyloxyphenol methoxyphenyl triazine | 2.0 |
| 18. Tripropylene glycol | 3.0 |
| 19. Purified water | 15.0 |

(Production Method)

A: Knead ingredients 1 to 6 using a three-roller mill

B: Heat and mix A and ingredients 7 to 16 at 50° C. to homogeneously disperse the ingredients C: Mix ingredients 17 to 19, add to B, and emulsify at normal temperature to obtain a liquid concentrate D: Load 9 g of the liquid concentrate obtained in C into a pressure-resistant container made from aluminum, subsequently fix a valve, and load 10 g of LPG0.15 and 2 g of dimethyl ether into the pressure-resistant container via the valve to obtain an aerosol foundation.

The aerosol foundation of Example 24 that was obtained as set forth above was a cosmetic lacking powder weight and oil weight, and having excellent cosmetic film uniformity while also having excellent dispersion stability.

Example 25: Water-in-Oil Liquid Foundation

| (Ingredient) | (%) |
|---|---|
| 1. Dimethicone-treated fine particulate titanium oxide (average particle diameter: 0.035 μm) | 4.0 |
| 2. Dimethicone-treated fine particulate zinc oxide (average particle diameter: 0.1 μm) | 2.0 |
| 3. Phospholipid-treated titanium (average particle diameter 0.4 μm) | 10.0 |
| 4. Dimethicone-treated red iron oxide powder (needle minor diameter: average particle diameter 0.07 μm) | 0.8 |
| 5. Dimethicone-treated yellow iron oxide powder (needle minor diameter: average particle diameter 0.09 μm) | 1.5 |
| 6. Dimethicone-treated black iron oxide powder (average particle diameter: more than 0.1 μm and not more than 0.3 μm) | 0.5 |
| 7. Dimethicone-treated talc (average particle diameter: 5 μm) | 2.0 |
| 8. Acrylates/ethylhexyl acrylate/dimethicone methacrylate copolymer *1 | 0.7 |
| 9. Methyl trimethicone | 3.0 |
| 10. Dimethylpolysiloxane (viscosity at 25° C.: 1.5 mm²/sec) | 5.0 |
| 11. Dimethylpolysiloxane (viscosity at 25° C.: 2.0 mm²/sec) | 7.0 |

-continued

| (Ingredient) | (%) |
|---|---|
| 12. Dimethylpolysiloxane (viscosity at 25° C.: 6 mm²/sec) | 5.0 |
| 13. Isotridecyl isononanoate | 3.0 |
| 14. Di(isostearyl/phytosteryl) dimer dilinoleate | 1.0 |
| 15. Trimethylsiloxysilicate | 2.0 |
| 16. Disteardimonium hectorite | 1.0 |
| 17. Sorbitan sesquiisostearate | 0.5 |
| 18. Lauryl PEG-9 polydimethylsiloxyethyl dimethicone | 3.0 |
| 19. PEG-9 polydimethylsiloxyethyl dimethicone | 3.0 |
| 20. 2-Ethylhexyl para-methoxycinnamate | 5.0 |
| 21. Diethylamino hydroxybenzoyl hexyl benzoate | 2.5 |
| 22. Bis-ethylhexyloxyphenol methoxyphenyl triazine | 0.5 |
| 23. Polymethylsilsesquioxane (average particle diameter: 5 μm) | 3.0 |
| 24. Spherical cellulose (average particle diameter: 1 μm) | 2.0 |
| 25. Silica (average particle diameter: 30 μm) | 1.0 |
| 26. Boron nitride | 2.0 |
| 27. Hydrogenated lecithin | 0.1 |
| 28. Ethanol | 5.0 |
| 29. 1,3-Butylene glycol | 1.0 |
| 30. Glycerin | 1.0 |
| 31. Purified water | Remainder |

(Production Method)

A: Homogeneously mix ingredients 1 to 11

B: Dissolve and mix ingredients 20 to 22 at 80° C., cool to room temperature, and subsequently add and disperse A and ingredients 12 to 19 and 23 to 27

C: Homogeneously mix ingredients 28 to 31

D: Add C to B, and emulsify and mix to obtain a water-in-oil liquid foundation

The water-in-oil foundation that was obtained as set forth above was a cosmetic lacking powder weight and oil weight, and having excellent cosmetic film uniformity while also having excellent dispersion stability.

Example 26: Aerosol Foundation

| (Ingredient) | (%) |
|---|---|
| 1. Stearic acid-treated fine particulate titanium oxide (average particle diameter: 0.035 μm) | 4.0 |
| 2. Dimethicone-treated fine particulate zinc oxide (average particle diameter: 0.035 μm) | 2.0 |
| 3. Disodium stearoyl glutamate-treated titanium oxide (average particle diameter: 0.25 μm) | 10.0 |
| 4. Dimethicone-treated red iron oxide powder (needle minor diameter: average particle diameter: 0.07 μm) | 0.8 |
| 5. Dimethicone-treated yellow iron oxide powder (needle minor diameter: average particle diameter 0.09 μm) | 1.5 |
| 6. Dimethicone-treated black iron oxide powder (average particle diameter: more than 0.1 μm and not more than 0.3 μm) | 0.5 |
| 7. Zinc laurate-treated talc (average particle diameter: 5 μm) | 2.0 |
| 8. Acrylates/ethylhexyl acrylate/dimethicone methacrylate copolymer *1 | 0.2 |
| 9. Methyl trimethicone | 3.0 |
| 10. Dimethylpolysiloxane (viscosity at 25° C.: 1.5 mm²/sec) | 5.0 |
| 11. Dimethylpolysiloxane (viscosity at 25° C.: 2.0 mm²/sec) | 7.0 |
| 12. Dimethylpolysiloxane (viscosity at 25° C.: 6 mm²/sec) | 5.0 |
| 13. Phytosteryl macadamiate | 3.0 |
| 14. Diisostearyl malate | 1.0 |
| 15. Trimethylsiloxysilicate | 2.0 |
| 16. Disteardimonium hectorite | 1.0 |
| 17. Sorbitan sesquiisostearate | 0.5 |
| 18. Lauryl PEG-9 polydimethylsiloxyethyl dimethicone | 3.0 |
| 19. PEG-9 polydimethylsiloxyethyl dimethicone | 3.0 |
| 20. 2-Ethylhexyl para-methoxycinnamate | 5.0 |
| 21. Diethylamino hydroxybenzoyl hexyl benzoate | 2.5 |
| 22. Bis-ethylhexyloxyphenol methoxyphenyl triazine | 0.5 |

-continued

| (Ingredient) | (%) |
|---|---|
| 23. Dimethicone/vinyl dimethicone crosspolymer | 3.0 |
| 24. Polymethylsilsesquioxane (average particle diameter: 5 μm) | 3.0 |
| 25. Spherical cellulose (average particle diameter: 5 μm) | 2.0 |
| 26. Silica (average particle diameter: 3 μm; oil absorption: 150 mL/100 g) | 1.0 |
| 27. Lauroyl lysine | 2.0 |
| 28. Hydrogenated lecithin | 0.1 |
| 29. Ethanol | 5.0 |
| 30. 1,3-Butylene glycol | 1.0 |
| 31. Glycerin | 1.0 |
| 32. Purified water | Remainder |

(Production Method)

A: Homogeneously mix ingredients 1 to 11

B: Dissolve and mix ingredients 20 to 22 at 80° C., cool to room temperature, and subsequently add and disperse A and ingredients 12 to 19 and 23 to 28

C: Homogeneously mix ingredients 29 to 32

D: Add C to B, and emulsify and mix to obtain a liquid concentrate

D: Load 6 g of the liquid concentrate obtained in D into a pressure-resistant container made from aluminum, subsequently fix a valve, and load 6 g of LPG0.15 and 0.5 g of carbon dioxide into the pressure-resistant container via the valve to obtain an aerosol foundation.

The aerosol foundation that was obtained as set forth above was a cosmetic lacking powder weight and oil weight, and having excellent cosmetic film uniformity while also having excellent dispersion stability.

Example 27: Impregnation-Type Foundation

| (Ingredient) | (%) |
|---|---|
| 1. Dimethicone-treated fine particulate titanium oxide (average particle diameter: 0.08 μm) | 10.0 |
| 2. Dimethicone-treated fine particulate zinc oxide (hexagonal plate shape; average particle diameter: 0.1 μm) | 5.0 |
| 3. Dimethicone-treated titanium oxide (average particle diameter: 1 μm) | 3.0 |
| 4. Dimethicone-treated red iron oxide powder (needle minor diameter: average particle diameter: 0.07 μm) | 0.8 |
| 5. Dimethicone-treated yellow iron oxide powder (needle minor diameter: average particle diameter 0.09 μm) | 1.5 |
| 6. Dimethicone-treated black iron oxide powder (average particle diameter: more than 0.1 μm and not more than 0.3 μm) | 0.5 |
| 7. Phospholipid-treated talc (average particle diameter: 5 μm) | 2.0 |
| 8. Acrylates/ethylhexyl acrylate/dimethicone methacrylate copolymer *1 | 1.5 |
| 9. Isododecane | 15.0 |
| 10. Dimethylpolysiloxane (viscosity at 25° C.: 6 mm²/sec) | 5.0 |
| 11. Isotridecyl isononanoate | 3.0 |
| 12. Diisostearyl malate | 1.0 |
| 13. Bis-isostearyl dimer dilinoleyl dimer dilinoleate | 2.0 |
| 14. Disteardimonium hectorite | 1.0 |
| 15. Sorbitan sesquiisostearate | 0.5 |
| 16. PEG-9 polydimethylsiloxyethyl dimethicone | 3.0 |
| 17. Polysilicone-15 | 4.0 |
| 18. 2-Ethylhexyl para-methoxycinnamate | 2.0 |
| 19. Diethylamino hydroxybenzoyl hexyl benzoate | 1.5 |
| 20. Bis-ethylhexyloxyphenol methoxyphenyl triazine | 0.5 |
| 21. Dimethicone/vinyl dimethicone crosspolymer | 3.0 |
| 22. Polymethylsilsesquioxane (average particle diameter: 5 μm) | 3.0 |
| 23. Spherical cellulose (average particle diameter: 15 μm) | 2.0 |
| 24. Silica (average particle diameter: 1 μm) | 1.0 |
| 25. Bismuth oxychloride | 2.0 |

| (Ingredient) | (%) |
|---|---|
| 26. Hydrogenated lecithin | 0.1 |
| 27. Ethanol | 5.0 |
| 28. 1,3-Butylene glycol | 1.0 |
| 29. Glycerin | 1.0 |
| 30. Purified water | Remainder |

(Production Method)

A: Homogeneously mix ingredients 1 to 9

B: Dissolve and mix ingredients 18 to 20 at 80° C., cool to room temperature, and subsequently add and disperse A and ingredients 10 to 17 and 21 to 26

C: Homogeneously mix ingredients 27 to 30

D: Add C to B, and emulsify and mix to obtain a foundation

E: Load bulk obtained in D into container in which NBR-type impregnation foam is supported to obtain a foundation The impregnation-type foundation that was obtained as set forth above was a cosmetic lacking powder weight and oil weight, and having excellent cosmetic film uniformity while also having excellent dispersion stability.

Example 28: Impregnation-Type Foundation

| (Ingredient) | (%) |
|---|---|
| 1. Dimethicone-treated fine particulate titanium oxide (average particle diameter: 0.05 μm) | 4.0 |
| 2. Dimethicone-treated fine particulate zinc oxide (average particle diameter: 0.05 μm | 2.0 |
| 3. Sodium dilauramidoglutamide lysine-treated titanium oxide (average particle diameter: 0.7 μm) | 10.0 |
| 4. Octyltriethoxysilane-treated red iron oxide powder (needle minor diameter: average particle diameter 0.07 μm) | 0.8 |
| 5. Octyltriethoxysilane-treated yellow iron oxide powder (needle minor diameter: average particle diameter 0.09 μm) | 1.5 |
| 6. Octyltriethoxysilane-treated black iron oxide powder (average particle diameter: 0.09 μm) | 0.5 |
| 7. Octyltriethoxysilane-treated talc (average particle diameter: 12 μm) | 2.0 |
| 8. Acrylates/ethylhexyl acrylate/dimethicone methacrylate copolymer *1 | 2.0 |
| 9. Methyl trimethicone | 3.0 |
| 10. Dimethylpolysiloxane (viscosity at 25° C.: 1.5 mm²/sec) | 5.0 |
| 11. Dimethylpolysiloxane (viscosity at 25° C.: 2.0 mm²/sec) | 7.0 |
| 12. Dimethylpolysiloxane (viscosity at 25° C.: 3.5 mm²/sec) | 5.0 |
| 13. Dipentaerythrityl 12-hydroxystearate/isostearate | 3.0 |
| 14. Diisostearyl malate | 1.0 |
| 15. Trimethylsiloxysilicate | 2.0 |
| 16. Disteardimonium hectorite | 1.0 |
| 17. Sorbitan sesquiisostearate | 0.5 |
| 18. Lauryl PEG-9 polydimethylsiloxyethyl dimethicone | 2.0 |
| 19. PEG-9 polydimethylsiloxyethyl dimethicone | 3.0 |
| 20. Polysilicone-15 | 5.0 |
| 21. Dimethicone/PEG-10/15 crosspolymer | 2.5 |
| 22. Dimethicone/polyglycerin-3 crosspolymer | 0.5 |
| 23. Dimethicone/vinyl dimethicone crosspolymer | 8.0 |
| 24. Polymethylsilsesquioxane (average particle diameter: 1 μm) | 3.0 |
| 25. Spherical cellulose (average particle diameter: 30 μm) | 2.0 |
| 26. Silica (average particle diameter: 20 μm) | 1.0 |
| 27. Glass powder | 2.0 |
| 28. Hydrogenated lecithin | 0.1 |
| 29. Ethanol | 5.0 |
| 30. 1,3-Butylene glycol | 1.0 |
| 31. Glycerin | 1.0 |
| 32. Purified water | Remainder |

(Production Method)

A: Homogeneously mix ingredients 1 to 11

B: Dissolve and mix ingredients 20 to 22 at 80° C., cool to room temperature, and subsequently add and disperse A and ingredients 12 to 19 and 23 to 28

C: Homogeneously mix ingredients 29 to 32

D: Add C to B, and emulsify and mix to obtain a foundation

E: Load bulk obtained in D into container in which polyether-type impregnation foam is supported to obtain a foundation The impregnation-type foundation that was obtained as set forth above was a cosmetic lacking powder weight and oil weight, and having excellent cosmetic film uniformity while also having excellent dispersion stability.

INDUSTRIAL APPLICABILITY

According to the present disclosure, it is possible to obtain a cosmetic excelling in terms of lack of powder weight, lack of oil weight, cosmetic film uniformity, and dispersion stability.

The invention claimed is:

1. A cosmetic comprising ingredients (A) to (C):
   (A) a metal oxide having an average particle diameter of 0.01 μm to 0.1 μm;
   (B) an oil that is a paste at 25° C. and that includes a hydrophilic group; and
   (C) an acrylates/ethylhexyl acrylate/dimethicone methacrylate copolymer, wherein
   the ingredient (B) is glycerin fatty acid esters and/or dimer acid esters,
   a mass content ratio of the ingredient (B) and the ingredient (C) is (B)/(C)=0.5 to 1.5, and
   a mass content ratio of the ingredient (A) and the ingredient (C) is (C)/(A)=0.1 to 1.

2. The cosmetic according to claim 1, wherein the ingredient (A) is one type or two or more types selected from titanium oxide and zinc oxide.

3. The cosmetic according to claim 1, wherein the ingredient (B) is phytosteryl/isostearyl/cetyl/stearyl/behenyl dimer dilinoleate, bis-diglyceryl polyacyladipate-2 or caprylic/capric/myristic/stearic triglyceride.

4. The cosmetic according to claim 1, wherein the cosmetic is a water-in-oil cosmetic.

5. The cosmetic according to claim 1, wherein the ingredient (B) is caprylic/capric/myristic/stearic triglyceride.

6. The cosmetic according to claim 5, wherein a mass content ratio of the ingredient (A) and the ingredient (B) is (A)/(B)=1.66 to 15.

* * * * *